United States Patent [19]

Ernst

[11] Patent Number: 4,899,578
[45] Date of Patent: Feb. 13, 1990

[54] DRIVING DEVICE FOR A HARDNESS MEASURING INSTRUMENT

[76] Inventor: Alfred Ernst, Via S. Martino, 6, Vezia Ticino, Switzerland

[21] Appl. No.: 162,866

[22] Filed: Mar. 2, 1988

[30] Foreign Application Priority Data

Mar. 18, 1987 [CH] Switzerland ............... 1029/87

[51] Int. Cl.$^4$ ............................................. G01N 3/42
[52] U.S. Cl. .......................................................... 73/82
[58] Field of Search ................................. 73/81–84; 74/190, 190.5, 840, 841, 424.8 R

[56] References Cited

U.S. PATENT DOCUMENTS 4,094,188 6/1978 Bellouin et al. ..................... 73/81

*Primary Examiner*—Michael J. Tokar
*Assistant Examiner*—Robert R. Raevis
*Attorney, Agent, or Firm*—Michael J. Striker

[57] ABSTRACT

A driving device for a hardness measuring instrument of the type including a fixed structure (2,3,4,5,6) having a base on which a piece to be controlled is firmly resting, and a movable assembly (7,8,9,10) that is driven from a motor (6) during a measuring cycle in such a manner as to be initially brought nearer the piece to be controlled and subsequently subjected to a measuring load, wherein the device utilizes, between the motor (6) and the movable assembly (7,8,9,10), two coaxial screws (11,13) having equally running threads, one of which screws is a large-pitch screw (11) and the other one is a small-pitch screw (13), the two screws being driven from the motor (6) and being arranged so that during a measuring operation, first the large-pitch screw (11) acts to cause the movable assembly (7,8,9,10) to be rapidly moved towards the piece to be controlled and then the small-pitch screw (13) acts to cause said movable assembly to be brought nearer said piece by a slow powerful motion, the reverse procedure taking place for returning the instrument (10) to its starting position.

23 Claims, 3 Drawing Sheets

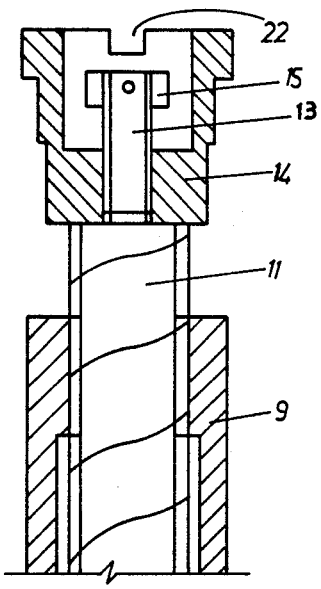
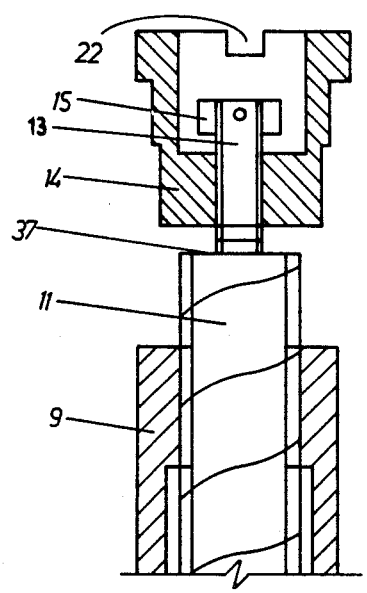
FIG.2    FIG.3
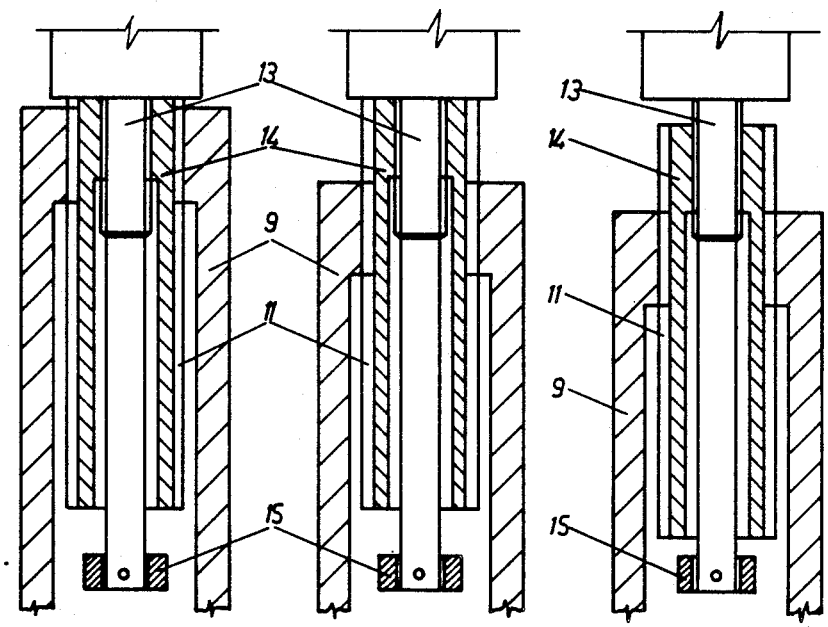
FIG.6    FIG.7    FIG.8

DRIVING DEVICE FOR A HARDNESS MEASURING INSTRUMENT

BACKGROUND OF THE INVENTION

This invention relates to a driving device for a hardness measuring instrument of the type including a fixed structure having a base member on which a piece to be measured is firmly resting, and a movable assembly comprising the measuring instrument proper, which is operated by a motor means during a measure cycle in such a manner as to be initially brought nearer the piece to be controlled and subsequently subjected to a measuring load.

In such hardness measuring instruments it is preferred that the instrument is moved rapidly but without any particular force toward a piece to be measured, and then pressed slowly but with considerable force against the piece, in order that reliable measurements can be obtained.

Once the required load is attained, the instrument is stopped and left in pressed condition under said load for a desired time, depending on the nature of the material of which the piece is made.

These hardness measuring instruments are usually operated by hydraulic means and are very much complicated in structure and, thus, subject to disadvantages.

For example, with these instruments, the above described type of handling is difficult to achieve and, as the stopping of the instrument at no time is instantaneous, due to the inertia of the driving means, a mismeasurement can be the result.

SUMMARY OF THE INVENTION

The object of this invention is to obviate the above-mentioned disadvantages by providing a driving device for hardness testing instruments which is of very simple conception and by which very reliable measurements can be performed.

The device according to the invention for driving a hardness measuring instrument of the type as described in the premise, is characterized in that provided between said motor means and said movable assembly are two coaxial screws having threads extending in the same directions, one of these screws being a large-pitch screw and the other one being a small-pitch screw and both screws being operated by the same motor means, these screws being arranged so that during a testing operation first the large-pitched screw acts to cause the instrument to move rapidly towards the piece to be measured and then the small-pitched screw acts to cause a slow but powerful advance of the instrument, the reverse procedure permitting the instrument to return to its starting position.

According to a preferred embodiment of the invention, the two coaxial screws are integral with, and disposed on the extension of one another with the screws being each engaged with respective nuts, the nut cooperating with the small-pitched screw being driven by the motor means while the nut cooperating with the large-pitched screw is attached to the movable part of the instrument.

According to another embodiment of the invention, the two coaxial screws are arranged inside one another, the small-pitched screw being driven by the motor means while the large-pitched screw engages with a nut attached to the movable part of the measuring instrument.

As a motor means for use in this invention, a motor reducer, with or without a brake, or a synchronous motor, or the like can be utilized. One advantage of the arrangement according to the invention is that it permits two speeds of translation of the measuring instrument to be obtained, without the speed of the motor having to be changed, which enables a considerable force, even at a small torque, to be applied on the controlled piece.

Another advantage is that, should the stopping of the motor not be instantaneous, due to inertia, any inaccuracy in stopping position and, thus, in the transmitted load, will be small in importance, owing to the very small-pitch of the small-pitched screw.

The above and further features and advantages of the invention will better appear when reading the following detailed description made with reference to the accompanying drawings which show by way of a non restrictive example one embodiment of the invention.

BRIEF DESCRIPTION OF THE DRAWINGS

FIGS. 2 and 3 are part sectional views showing the device for driving the movable assembly of the instrument in FIG. 1, in different positions as taken by the device during a measuring cycle;

FIGS. 6, 7 and 8 show, in sectional views, the components of the device for driving the movable assembly of the measuring instrument in three different positions as taken during a measuring cycle, said components being constructed according to a modified embodiment of the invention.

DESCRIPTION OF THE PREFERRED EMBODIMENT

Figure 1:
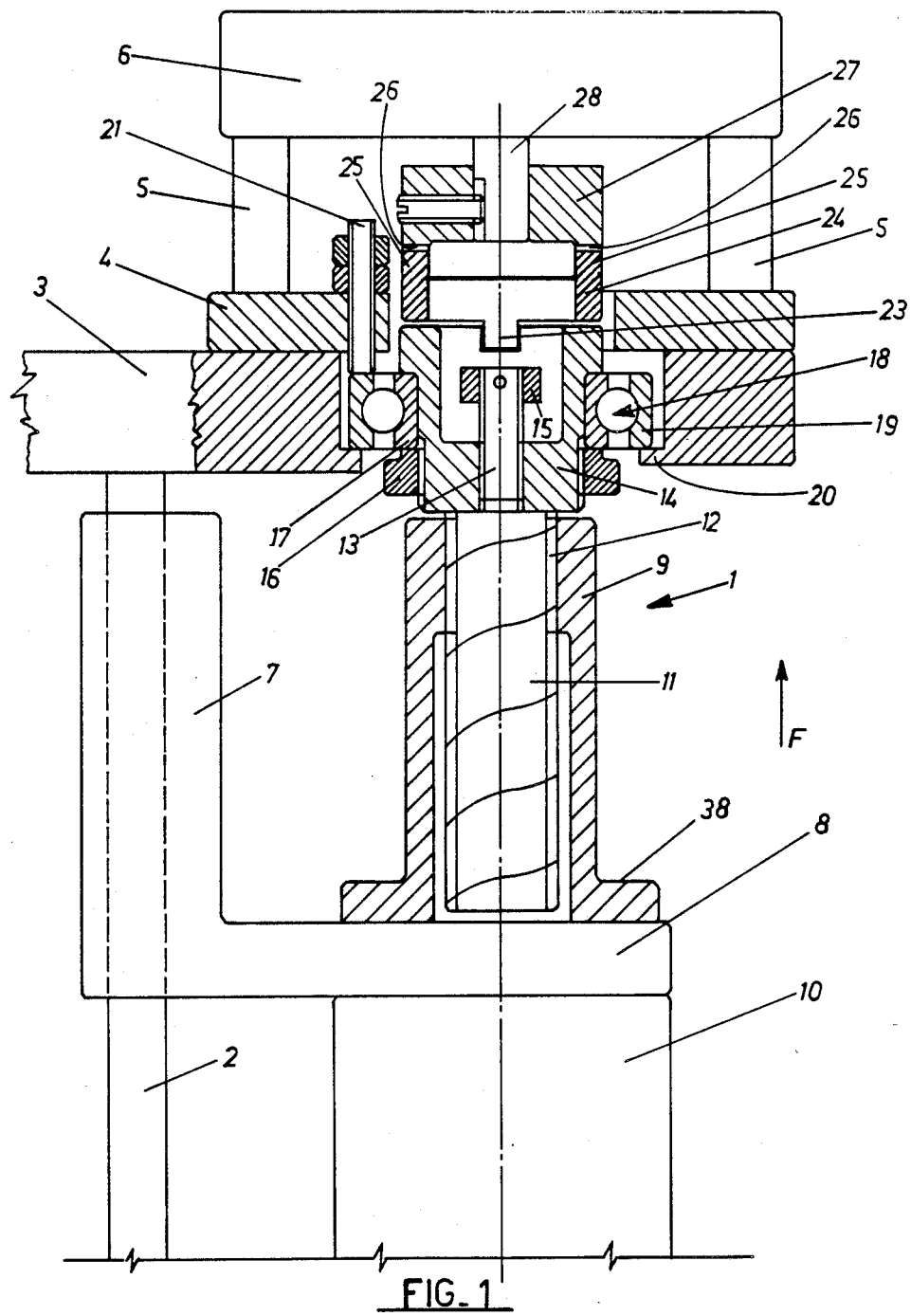
FIG. 1 is a middle cross-sectional view showing a driving device according to a preferred embodiment of the invention, the device being mounted on a hardness test instrument of which only an upper part is shown in a partial schematic manner.

Referring now first to FIG. 1, generally designated by numeral 1 is a hardness measuring instrument including a driving device according to a preferred embodiment of this invention. The instrument 1 is shown to have a vertical axis since the vertical position corresponds to its usual position of use, though other positions of utilisation of the instrument 1 are also possible, as will be explained further.

FIG. 1 schematically shows in outline only an upper part of the measuring instrument 1 since this is the part enclosing the basic elements of the invention.

The measuring instrument 1 consists of a fixed structure on a lower base (not shown in the figure) of which a piece to be tested is firmly resting, and an assembly which is movably mounted with respect to the fixed structure and which includes the measuring instrument.

In FIG. 1, the fixed structure of the measuring instrument is shown to include a vertical guide 2, a horizontal plate 3 provided at the top of guide 2, a second horizontal plate 4, vertical columns 5 extending from the plate 4 and topped by a motor means 6 which may for example be a motor reducer or a synchronous motor. Thus, all of the elements 2,3,4,5 and 6 are rigidly locked with each other.

The movable assembly of the measuring instrument 1 comprises a slider 7 which is vertically slidable, with little friction, along the guide 2 and which has a horizontal arm 8 supporting at its top a nut 9 to be described in more details further, and, at its underside, the measuring instrument proper 10, of which only an upper part is shown, since it does not form a specific subject of this invention. Thus, all of the elements 7, 8, 9 and 10 are rigidly locked with each other. The nut 9 the axis of which is coincident with the axis of the instrument, has a large-pitch screw 11 engaged therewith. The effective length of nut 9, that is the length of its internally threaded portion 12, should preferably be at least the same as the pitch of the thread on screw 11, when this is a single-threaded screw.

Axially arranged above, and fast with the large-pitch screw 11, is a small-pitch screw 13 engaging a nut 14 and having at its top a stop 15 for preventing any working-loose condition. This stop 15 is inoperative during operation of the device and serves only as a safety means for preventing the movable assembly 7, 8, 9 and 10 from falling off if the screw 13 completely disengages from its nut 14.

The nut 14 is rigidly locked by the aid of a metal ring 16 with the inside race or ring 17 of a ball bearing 18 which is designed to support also axial loads and the outer race 19 of which rests on a lip 20 formed in the plate 3.

Three screws 21 (only one being shown in sectional view, FIG. 1) are passed through plate 4 to abut against the top face of the outer race 19 of bearing 18 thereby preventing this latter from moving axially but without locking it in place, so that small side-movements of this bearing are allowed and permit self-centering action thereof.

Formed in the top of nut 14, which is cup-shaped, are two diametrically opposed notches 22 (only one shown, FIGS. 1,2,3) which receive two corresponding projections 23 extending from a bottom part of a ring 24. This ring 24 has at its top two further projections 25 being arranged at 90° with respect to the bottom projections 23 and fitting into corresponding notches 26 (see FIG. 1) in a bottom part of a hub 27 rigidly locked to a shaft 28 of motor 6.

These thus shaped and arranged elements form together a coupling means through which the rotary motion of shaft 28 can be transmitted to the nut 14 even when those elements would be not very accurately aligned with each other as it generally occurs in the practice.

As it should be apparent from the above description, the nut 14 is unable to do axial movements and is only capable of rotating with small side-movements thereof being allowed, such that this nut 14 may be considered as making a part of the fixed structure 2, 3, 4, 5, 6 of the device.

Figure 5:
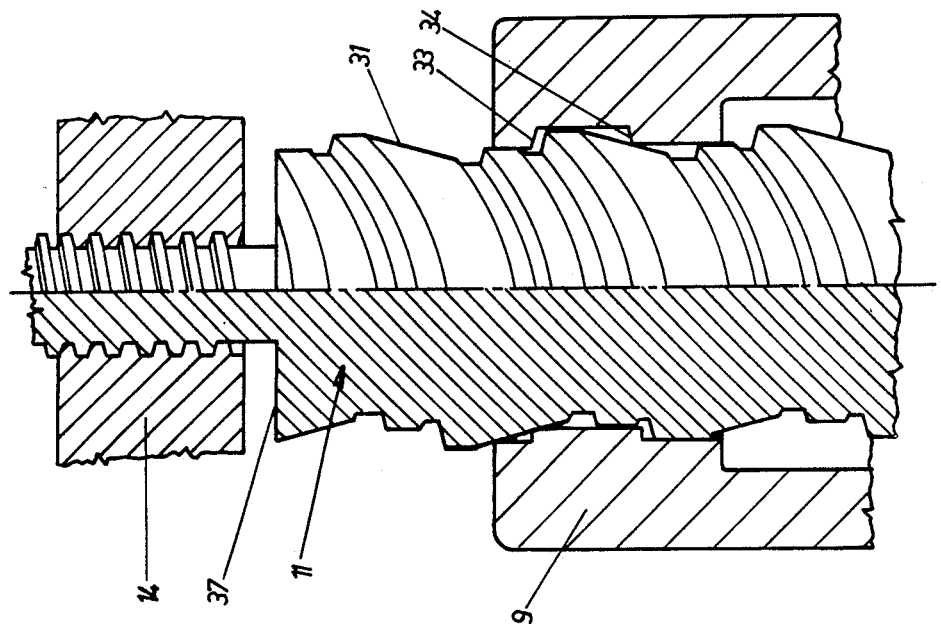
FIGS. 4 and 5 are part sectional views showing, on a larger scale, the components of the driving device illustrated in FIGS. 1, 2 and 3, the positions corresponding to those in FIGS. 1 and 2 respectively.
Figure 4:
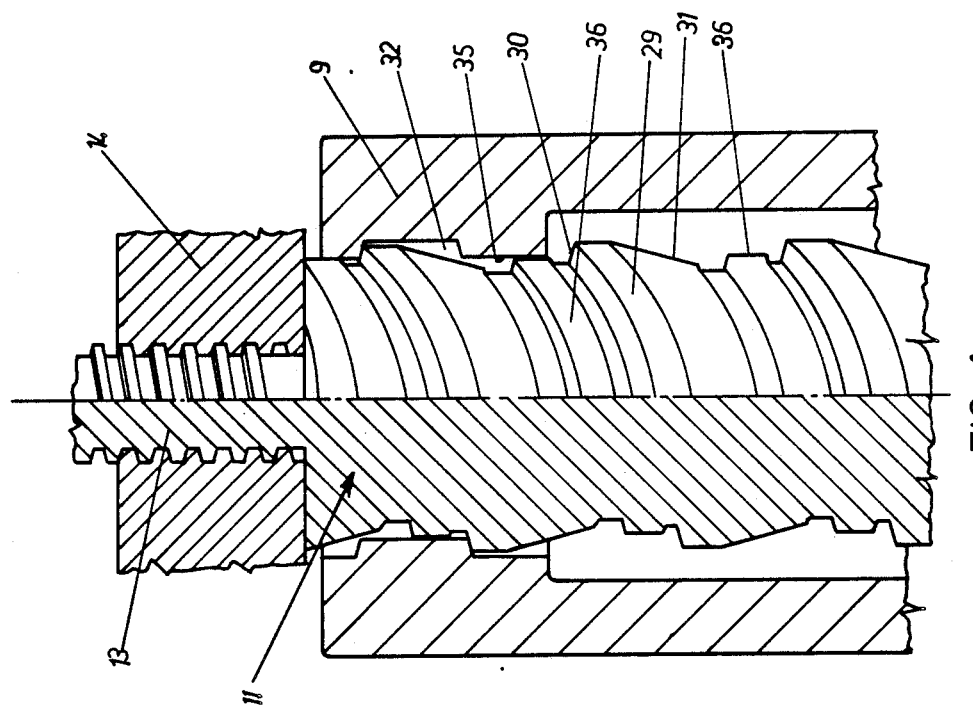

Before describing operation of the driving device for hardness measuring instruments according to the invention, it is to be noted that the screws 11 and 13 have the same direction of screwing, for example, they are both right-handed screws and, advantageously, the large-pitch screw 11 and the associated nut 9 have the peculiarly shaped thread profiles as shown in FIGS. 4 and 5 and explained herein below.

Referring now to FIGS. 4 and 5, it can be seen that the large-pitch screw 11 has a steeply sloping helix 29.

Further with reference to FIGS. 4 and 5, the upper profile 30 of helix 29 is slightly sloping with respect to a plane perpendicular to the axis of screw 11, while the lower profile 31 of helix 29 is steeply sloping with respect to said plane.

The nut 9 has a flat bottomed, recessed helix 32 cut inside the nut, said helix 32 being bounded at the top by a profile 33 matchingly fitting the upper profile 30 of helix 29 on screw 11, and, at the bottom, by a profile 34 designed to interfere with the lower profile 31 of helix 29.

The profiles 33 and 34 terminate on the internal cylinder surface 35 of the concerned nut which surface is abutting against the outer profile 36 of a second helix of reduced diameter, that is formed on the screw 11 with the purpose of holding this screw 11 in a centered position, taking into account that said screw is free to set laterally to some extent, as mentioned before.

As seen when comparing FIGS. 4 and 5, the nut 9 has a small end play with respect to screw 11. Thus, FIG. 4, when the nut 9 works in a downward direction, with respect to the screw 11, due to its own weight and the weights of slider 7 and measuring instrument 10 attached thereto, the nut 9 thoroughly bears by its profile 33 on thread profile 30 of screw 11. Under this condition, owing to the low friction between the parts (which is due to the presence of lubricant oil, if any) and thanks to the steep sloping of the screw helix, the screw has no self-stopping. In other words—FIG. 4—assuming for a moment that the nut 9 would be enabled to rotate with respect to the screw 11 (and not the reverse condition as it occurs during operation of the device), by having the screw 11 held against movement, then the nut 9 would tend to rotate around the screw 11 by action of gravity only.

On the other hand, when the nut 9 is working in a upward direction (FIG. 5), the profile 34 of said nut will interfere with the sloping profile 31 of the screw 11, as a result of which a self-stopping is obtained. More precisely, assuming the truth of the imaginary condition as described above, if an axial upward force is applied to the nut 9, this latter would in any case remain locked on the screw 11 so that it is necessary to rotate the nut to cause it to advance.

Now, operation of the driving device for a hardness test instrument according to the invention will be described below with reference to FIGS. 1 to 5.

FIGS. 1 and 4 show the movable components of the device when at the top dead center position, that is, at the start of a measurement cycle. In this position, the base of the fixed structure of the instrument—which is supposed to work vertically downwards—has the piece to be controlled stationarily resting thereon, while the measuring instrument 10 making a part of the movable assembly of said instrument, is held in an elevated and, thus, spaced apart position with respect to the surface of the controlled piece.

Under this condition, the small-pitch nut 14 is at the end of its stroke and is abutting by its lower part against an upper shoulder 37 on the large-pitch screw 11, whose diameter is larger than that of screw 13.

In this situation, owing to what mentioned before, the screw 11 has no self-stopping so that, under the weight of the associated nut 9 and the members attached thereto, it tends to rotate slightly thus holding the nut 14 in its end-of-stroke position.

It is intended that the directions of rotation are as seen when looking at the instrument from below it, and along the axis thereof, i.e. in the way indicated by the arrow F, FIG. 1, which also applies to all of the other figures.

Now, in the position shown FIGS. 1 and 4 the screw 11 tends to rotate clockwise. In any case, the friction proper of the motor reducer, or the effect produced by the permanent magnets, if a synchronous motor 6 is used, is sufficient to prevent the driving shaft 28 from being set in rotation.

When a measurement has to be effected, the driving shaft 28 is caused to rotate clockwise at constant speed so that the nut 14 is driven into rotation through the coupling 24. Initially, the large-pitch screw will also rotate together with the nut 14 since, as already said, the screw 11 is held in abutting relationship with the nut 14.

The rotation of the screw 11 causes the nut 9 and, thus, the entire assembly attached to the slider 7 and including the measuring instrument 10, to move fast downwardly.

When the descending instrument 10 will come to a point where it rests on the surface of the piece to be measured (see FIG. 2), the nut 9 moves out of contact with the profile 30 of screw 11, on which it was previously resting, to bring its profile 34 into interference contact with the sloping profile 31 of screw 11 and to be locked there (see also FIG. 5).

At that time, the screw 11 and the associated nut 9 become locked with one another so that the nut 14 will continue to rotate around the associated small-pitch screw 13 to cause its moving away from the shoulder 37 of the large-pitch screw 11 (see FIGS. 3 and 5).

Thus, during this step, it is the small-pitch screw 13 rigidly locked with the screw 11 that will urge the entire assembly downwardly at a lower speed but with substantial force.

When, in a manner known per se, a stopping signal from the instrument is applied to the motor means 6, this motor is stopped and the measuring instrument 10 remains pressed against the measured piece with the proper load and for a properly-set time depending on the type of material being tested.

When a measuring cycle has come to an end, the motor 6 is caused to rotate anticlockwise. During this step, the nut 14 regains its end-of-stroke position by rotation around the small-pitch screw 13 to pass from position FIG. 3 to position FIG. 2, at which time it transmits the rotation to the large-pitch screw 11 on the profile 30 of which the nut 9 is resting. As a result, the entire movable assembly including the instrument 10 is moved upwards to the top dead center position shown in FIGS. 1 and 4, in which position the motor means 6 is stopped.

In a very particular case where, in order to effect a measuring operation, the instrument has to work horizontally or even in a direction going from bottom to top, the device of the invention can also be utilized provided that a means should be used which acts as a substitute for the gravitional force to urge the entire movable assembly toward the surface to be controlled. For example, a spring means may be provided which works between the movable assembly and the fixed structure of the measuring apparatus 1; in particular, the spring means may be a helical-type compression spring wound around the nut 9 so as to bear on a shoulder 38 of the movable assembly and to react against the lower surface of plate 3 of the fixed structure (see FIG. 1).

FIGS. 6, 7 and 8 show a modified embodiment of the driving means for the movable assembly of the hardness measuring instrument 1 according to the invention.

In these figures the same reference numerals as those in FIGS. 1 to 5 are used for designating the same elements, or elements performing the same functions.

In particular, according to this modified embodiment, the small-pitch screw 13 is coaxially received inside the large-pitch screw 11 and threadingly engages the nut 14 which is made integral with the screw 11. The large-pitch nut 9 is unchanged and the profile thereof as well as the profile of the large-pitch screw 11 are again as shown in FIGS. 4 and 5. In this case, the small-pitch screw 13 is driven directly by the motor means 6 and, thus, it performs the same function as does the nut 14 of the embodiment in FIGS. 1 to 5. The stop 15 on screw 13 is in this case arranged at the lowest end of this screw. Operation of the device is identical to that described in relation to FIGS. 1 to 5, so that it will be described in short only.

The position shown in FIG. 6 corresponds to the top dead center position at the beginning of a cycle. By rotation of the motor 6 and, thus, the small-pitch screw 13, in a clockwise direction, first the small-pitch nut 14 and the large-pitch screw 11 (integral therewith) are driven in rotation, as a result of which the large-pitch nut 9 is moved downwards to a position as shown FIG. 7. In this position, the instrument is bearing on the surface of the piece to be controlled, whereby the large-pitch nut 9 is urging upwardly and will be locked on the large-pitch screw 11. As the motor means continues to rotate, the screw 13 rotates in the nut 14 (which is integral with the screw 11) to cause it to move downwards together with the entire movable assembly at a reduced speed, until the position in FIG. 8 is reached.

The return of the instrument to a rest position takes place in a same manner by reversing the direction of rotation of motor 6 to pass from position FIG. 8 to position FIG. 7 and then to the position in FIG. 6 corresponding to the top dead center position.

As a matter of fact, in addition to the embodiments shown, other equivalent embodiments may be provided and will fall within the scope of this invention.

A particular profile has been preferably chosen for the large-pitch screw 11 and the associated nut 9 such that the screw will have spontaneous stoppage only when the nut is urging toward one direction and not toward the other one, in order to avoid recourse to auxiliary means for obtaining the same effects, which auxiliary means are, therefore, intended as being covered by the invention.

Thus, for example, the large-pitch screw 11 and its nut 9 may have threads of strictly conventional profiles, and such for example as the threads on the small-pitch screw 13 and the associated nut 14, as long as a coupling means is provided, for example, of the dovetail-joint type, which causes the nut 14 (FIGS. 1 to 5) or the screw 13 (FIGS. 6 to 8) to occupy its end-of-stroke position, respectively. Such a coupling means enables, at an initial stage of the measurement cycle, to drive the large-pitch screw into rotation and, thereafter, upon disconnection of the coupling, to cause the small-pitch screw 13 to operate.

Though the invention has been particularly described in relation to its application to a hardness measuring instrument, it should be apparent that it could be applied as well to any other machine, device or instrument wherein a member has to be initially subjected to a fast motion without any particular force being implied, and then to a slow motion with considerable force involved.

Obviously, the invention is not restricted to the particular embodiments thereof that have been disclosed herein before and shown by the accompanying drawings, and many modifications as to the details of construction may be thought by those skilled in the art without departing from the spirit and scope of the invention.

I claim:

1. A driving device of a hardness measurement arrangement, comprising:
    a fixed structure (2-6) with a base member on which a piece to be measured is to rest;
    a movable assembly (7-10);
    motor means (6) for driving the movable assembly (7-10) during a measuring cycle; and
    two screws including a small pitch screw (13) and a large pitch screw (11) having a pitch larger than that of the small pitch screw, the two screws having threads wound in the same direction and being arranged between the motor means (6) and the movable assembly (7-10), the two screws being responsive to the motor means so that during the measuring cycle, the large-pitch screw advances the movable assembly rapidly toward the piece to be measured and the small-pitch screw subsequently causes the movable assembly to perform a slower and more powerful advance than before, the screws being further responsive to the motor means so that the movable assembly is returned to a starting position by the small-pitch screw retracting the movable assembly first and followed by the large-pitch screw retracting the movable assembly thereafter.

2. The device as defined in claim 1, wherein the movable assembly includes a hardness measuring instrument (10).

3. The device as defined in claim 1, wherein the two screws are coaxial with each other.

4. The device according to claim 1, wherein the two screws (13 and 11) are arranged inside one another, the small-pitch screw (13) being driven by the motor means (6), and further comprising:
    a small-pitch nut (14) integral with the large-pitch screw (11) and engaging the small-pitch screw (13); and
    a large-pitch nut (9) rigidly locked with the movable assembly (7,8,9,10) and engaging the large pitch screw.

5. The device according to claim 4, wherein the large-pitch screw (11) and the large-pitch nut (9) have a thread profile which is such that the large-pitch screw (11) will have spontaneous stoppage for only one direction of axial thrust of the large-pitch nut (9) and not for the other direction thereof.

6. The device according to claim 5, wherein the large-pitch screw (11) has a screw axis and a steeply sloping helix with a top and a bottom, the helix being bounded at the top by a thread profile (30) slightly sloping with respect to a plane orthogonal to the screw axis and, at the bottom by a sloping profile (31) steeply sloping with respect to the plane, the large-pitch nut (9) having an internal thread profile (33) exactly fitting the thread profile (30) of the large-pitch screw and a profile (34) arranged to interfere with the sloping profile (31).

7. The device according to claim 6, wherein the large-pitch screw (11) has a second helix (36) with an outer profile and being of reduced diameter with respect to the steeply sloping helix (29), the large-pitch nut (9) having an internal cylindrical surface (35) abutting the outer profile of the second helix (36).

8. The device according to claim 1, further comprising:
    a driving shaft (28) rotatably driven by the motor means; and
    joint means (24) for transmitting rotation of the driving shaft (28) to the small-pitch screw (13) even if the driving shaft (28) and the small-pitch screw (13) are not aligned with one another.

9. The device according to claim 1, further comprising:
    a driving shaft (28) rotatably driven by the motor means; and
    joint means (24) for transmitting rotation of the driving shaft (28) to the small-pitch nut (14) even if the driving shaft (28) and the small-pitch nut (14) are not aligned with one another.

10. The device according to claim 1, and further comprising:
    a ball bearing (18) axially supporting the small-pitch screw (13), the ball bearing (18) being axially locked with the fixed structure (2,3,4,5,6).

11. The device according to claim 1, wherein a spring means is provided to work between the movable assembly (7,8,9,10) and the fixed structure (2,3,4,5,6).

12. The device according to claim 1, and further comprising:
    a ball bearing (18) axially supporting the small-pitch nut (14), the ball bearing (18) being axially locked with the fixed structure (2,3,4,5,6).

13. The device according to claim 1, and further comprising:
    a small-pitch nut (14) engaging and cooperating with the small-pitch screw (13); and
    a large-pitch nut (9) engaging and cooperating with the large-pitch screw (11), the small-pitch screw (13) being driven by the motor means (6), while the large-pitch nut (9) is rigidly locked with the movable assembly (7,8,9,10).

14. The device according to claim 13, and further comprising:
    a ball bearing (18) axially supporting the small-pitch nut (14), the ball bearing (18) being axially locked with the fixed structure (2,3,4,5,6).

15. The device according to claim 13, wherein the large-pitch screw (11) and the large-pitch nut (9) have a thread profile which is such that the large-pitch screw (11) will have spontaneous stoppage for only one direction of axial thrust of the large-pitch nut (9) and not for the other direction thereof.

16. The device according to claim 13, wherein a spring means is provided to work between the movable assembly (7, 8, 9, 10) and the fixed structure (2, 3, 4, 5, 6).

17. The device according to claim 13, and further comprising:
    a ball bearing (18) axially supporting the small-pitch screw (13), the ball bearing (18) being axially locked with the fixed structure (2,3,4,5,6).

18. The device according to claim 1, wherein a stop means (15) is provided on a free end of the small-pitch screw (13).

19. The device according to claim 18, wherein said motor means (6) is formed as a motor reducer.

20. The device according to claim 19, wherein said motor (6) is formed to operate at a constant speed.

21. The device according to claim 18, wherein the motor means (6) is formed as a synchronous motor.

22. The device as defined in claim 1, wherein the small-pitch screw (13) and the large screw (11) are disconnectably coupled with one another so as to control operations of the two screws (11, 13) during the operation of the motor means (6).

23. A driving device of a hardness measurement arrangement, comprising:
a fixed structure;
a movable member;
screw means for driving the movable member relative to the fixed structure during a measurement cycle; and
motor means for driving the screw means, the screw means including two screws (11, 13) having differently pitched threads that are wound in the same direction, one of the screws being formed for initially driving the movable member quickly to provide a moderate force and the other of the screws being formed for subsequently driving the movable member slowly to provide a stronger force.

* * * * *